US008701471B2

(12) United States Patent
O'Donnell et al.

(10) Patent No.: US 8,701,471 B2
(45) Date of Patent: Apr. 22, 2014

(54) METHOD AND SYSTEM FOR BACKGROUND SUPPRESSION IN MAGNETO-MOTIVE PHOTOACOUSTIC IMAGING OF MAGNETIC CONTRAST AGENTS (75) Inventors: Matthew O'Donnell, Seattle, WA (US); Xiaohu Gao, Shoreline, WA (US)

(73) Assignee: University of Washington through its Center for Commercialiation, Seattle, WA (US)

( * ) Notice: Subject to any disclaimer, the term of this patent is extended or adjusted under 35 U.S.C. 154(b) by 278 days.

(21) Appl. No.: 13/273,095

(22) Filed: Oct. 13, 2011

(65) Prior Publication Data

US 2012/0118052 A1    May 17, 2012

Related U.S. Application Data (63) Continuation-in-part of application No. PCT/US2010/041421, filed on Jul. 8, 2010.

(60) Provisional application No. 61/392,927, filed on Oct. 13, 2010, provisional application No. 61/270,476, filed on Jul. 8, 2009, provisional application No. 61/349,170, filed on May 27, 2010.

(51) Int. Cl.
*G01N 29/02* (2006.01)
*A61B 5/05* (2006.01)

(52) U.S. Cl.
USPC .......................... 73/64.53; 600/407

(58) Field of Classification Search
USPC ........ 73/64.53, 54.14, 54.15, 54.18; 600/407, 600/424
See application file for complete search history.

(56) References Cited

U.S. PATENT DOCUMENTS

| 6,100,687 | A  | * | 8/2000 | Weitekamp et al. | 324/300 |
|---|---|---|---|---|---|
| 8,119,165 | B2 | * | 2/2012 | Peyman | 424/489 |
| 8,317,737 | B2 | * | 11/2012 | Hyde et al. | 604/4.01 |
| 8,481,082 | B2 | * | 7/2013 | Peyman | 424/489 |
| 2005/0025969 | A1 | | 2/2005 | Berning | |
| 2006/0057384 | A1 | | 3/2006 | Simard | |
| 2006/0140868 | A1 | | 6/2006 | Grancharov | |
| 2008/0145660 | A1 | | 6/2008 | Wang | |
| 2009/0322327 | A1 | | 12/2009 | Gao | |
| 2010/0069550 | A1 | | 3/2010 | Gao | |
| 2011/0117028 | A1 | | 5/2011 | Zharov | |
| 2012/0201361 | A1 | * | 8/2012 | Angel et al. | 379/88.01 |
| 2012/0302866 | A1 | * | 11/2012 | Fukutani et al. | 600/407 |
| 2013/0190591 | A1 | * | 7/2013 | Hirson et al. | 600/407 |
| 2013/0217995 | A1 | * | 8/2013 | Kruger | 600/407 |

FOREIGN PATENT DOCUMENTS

WO    2011/006002 A2    1/2011
WO    2011/143128 A2    11/2011

OTHER PUBLICATIONS

Magnetomotive Photoacoustic imaging, J. Biophotonics 6, Wei et al. 2013.*
Galanzha, E.I, et al., "In Vivo Magnetic Enrichment and Multiplex Photoacoustic Detection of Circulating Tumour Cells," Nature Nanotechnology 4(12):855-860, Dec. 2009.
International Search Report mailed Feb. 28, 2011, issued in corresponding International Application No. PCT/US2010/041421, filed Jul. 8, 2010, 11 pages.

(Continued)

*Primary Examiner* — J M Saint Surin
(74) *Attorney, Agent, or Firm* — Christensen O'Connor Johnson Kindness PLLC (57) ABSTRACT

Method and system for background suppression in magneto-motive photoacoustic imaging of labeled target objects.

47 Claims, 7 Drawing Sheets

(56) References Cited

OTHER PUBLICATIONS

Jin, Y., and X. Gao, "Plasmonic Fluorescent Quantum Dots," Nature Nanotechnology 4(9):571-576, Sep. 2009.

Kim, J., et al., "Imaging Nanoparticle Flow Using Magneto-Motive Optical Doppler Tomography," Nanotechnology 18(3):035504, Jan. 2007, 6 pages.

Oh, J., et al., "Detection of Magnetic Nanoparticles in Tissue Using Magneto-Motive Ultrasound," Nanotechnology 17(16):4183-4190, Aug. 2006.

Oh, J., et al., "Magneto-Motive Detection of Tissue-Based Macrophages by Differential Phase Optical Coherence Tomograph," Lasers in Surgery and Medicine 39(3):266-272, Mar. 2007.

* cited by examiner

METHOD AND SYSTEM FOR BACKGROUND SUPPRESSION IN MAGNETO-MOTIVE PHOTOACOUSTIC IMAGING OF MAGNETIC CONTRAST AGENTS

CROSS-REFERENCES TO RELATED APPLICATIONS

This application claims the benefit of U.S. Patent Application No. 61/392,927, filed Oct. 13, 2010, and is a continuation-in-part of International Patent Application No. PCT/US2010/041421, filed Jul. 8, 2010, which claims priority to U.S. Patent Application No. 61/270,476, filed Jul. 8, 2009, and U.S. Patent Application No. 61/349,170, filed May 27, 2010, each of which is expressly incorporated herein by reference in its entirety.

STATEMENT OF GOVERNMENT LICENSE RIGHTS

This invention was made with Government support under Contract Nos. RO1 CA131797 and RO1 CA140295 awarded by the National Institutes of Health, and under Contract No. 0645080 awarded by the National Science Foundation. The Government has certain rights in the invention.

BACKGROUND OF THE INVENTION

Photoacoustic (PA) imaging is based on the detection of acoustic signals induced by the distribution of specific optical heterogeneities in targeted objects when irradiated by short laser pulses. Contrast in PA images is primarily determined by optical absorption, but spatial resolution is the same as in ultrasound. This contrast capability within deep biological tissue cannot be achieved by pure optical or ultrasound imaging, which both depend primarily on wave scattering mechanisms. Given the megahertz (MHz) range of acoustic signals processed in PA imaging, sub-millimeter resolution is possible for routine clinical applications.

Photoacoustics is very attractive for molecular imaging because optical absorption is an efficient way to detect and differentiate specific molecules from other components. By designing a specific wavelength selective absorption contrast agent, PA imaging can provide high sensitivity and specificity to molecular targets. By coupling specifically designed molecular contrast agents to particular biological objects such as cancer cells, targeted cells can be specifically differentiated from the background.

However, when visualization of targeted molecules is necessary in the vasculature, PA imaging is severely challenged by the large optical absorption of hemoglobin even within the therapeutic window of optical radiation. The strong PA background signal from blood can mask contrast agents and make quantitative measurements of molecular concentration very difficult, especially for low concentrations of contrast agents.

The PA signal from a targeted contrast agent can be increased relative to the background by increasing its concentration, especially in model systems such as mice, but in humans potential toxicity limits increases in contrast agent concentration. Furthermore, in certain applications, such as in rare cell detection, this is not feasible. Indirect enhancement of the PA signal from the targeted object is much more desirable.

One method to suppress the background relative to a targeted contrast agent is to use PA measurements at multiple wavelengths to differentiate the contrast agent absorption signature from that of the background. Promising results have been achieved recently in multicolor PA tomography. The main drawback of this approach is the difference in light scattering at different wavelengths. In particular, the distribution of laser fluence inside the object under study cannot be considered the same at different wavelengths. This makes solution of the inverse problem quite ambiguous.

U.S. Patent Application Publication No. US 2011/0117028 describes a two-wavelength approach using multiple contrast agents to identify magnetically trapped circulating tumor cells using PA imaging. However, such an approach will be difficult to translate into the clinic because it uses multiple types of nanoparticles and a multi-wavelength system requiring careful in situ calibration to ensure sufficient suppression of the background blood signal.

Despite the advances in photoacoustic imaging noted above, a need exists to provide a method and device for suppressing background signal in magneto-motive photoacoustic imaging of magnetic contrast agents in complex systems. The present invention seeks to fulfill this need and provides further related advantages.

SUMMARY OF THE INVENTION

The present invention provides a method and system for magneto-motive photoacoustic (mmPA) imaging that utilizes nanoparticles with combined strong magnetic and efficient optical absorption properties. The method and system provide for magneto-motive manipulation to differentiate a coupled contrast agent from background signals.

In one aspect, the invention provides a method for imaging magnetic target objects within a moving fluid. In one embodiment, the method includes (a) introducing a plurality of magnetic particles having photoacoustic properties to a moving fluid comprising target objects to provide magnetically-labeled target objects;

(b) applying a magnetic field to an area of interest through which the fluid flows to accumulate the magnetically-labeled target objects in the area of interest to provide accumulated magnetically-labeled target objects in a first position;

(c) measuring a first photoacoustic signal from the accumulated magnetically-labeled target objects in the first position;

(d) manipulating the magnetic field in the area of interest to move at least a portion of the accumulated magnetically-labeled target objects in a predetermined pattern directly related to the magnetic field manipulation; and (e) measuring one or more photoacoustic signals from the accumulated magnetically-labeled target objects during and after magnetic field manipulation.

In one embodiment, measuring one or more photoacoustic signals from the accumulated magnetically-labeled target objects during and after magnetic field manipulation includes measuring a sequence of photoacoustic signals from the accumulated magnetically-labeled target objects during and after magnetic field manipulation.

In one embodiment, the method further includes comparing the sequence of photoacoustic signals during magnetic field manipulation to provide a background suppressed photoacoustic signal. Comparing the sequence of photoacoustic signals during magnetic field manipulation provides a background suppressed photoacoustic image of the accumulated magnetically-labeled target objects.

In one embodiment, manipulating the magnetic field provides for the acquisition of photoacoustic signals from the accumulated magnetically-labeled target objects at two separate spatial locations. In this embodiment, comparing the photoacoustic signals acquired from the accumulated magnetically-labeled target objects at two separate spatial locations provides a background suppressed photoacoustic signal. Comparing the photoacoustic signals acquired at two separate spatial locations provides a background suppressed photoacoustic image of the accumulated magnetically-labeled target objects.

In certain embodiments, the method further includes subjecting the accumulated magnetically-labeled target objects to an additional process selected from removal for biochemical or genetic analysis; non-invasive eradication using high-energy pulses selected from laser pulses, microwave pulses, or ultrasound pulses; magnetic purging; mechanical removal; needle extraction; or any combination thereof.

In another aspect of the invention, a system for imaging magnetic target objects within a moving fluid. In one embodiment, the system includes (a) one or more first magnets effective for establishing a magnetic field in an area of interest within moving fluid containing magnetically-labeled target objects;

(b) one or more second magnets effective for establishing a magnetic field including both a polarizing field and gradient fields in an area of interest within moving fluid containing magnetically-labeled target objects;

(c) one or more energy sources for delivering incident energy to the accumulated magnetically-labeled target objects in the area of interest; and (d) one or more photoacoustic transducers for receiving the photoacoustic signal from the accumulated magnetically-labeled target objects.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this invention will become more readily appreciated as the same become better understood by reference to the following detailed description, when taken in conjunction with the accompanying drawings.

In FIG. 1A, the magnetically-labeled target objects are accumulated at a first position. In FIG. 1B, the magnetically-labeled target objects are accumulated at a second position.

FIGS. 3A-3B are photoacoustic images (logarithmic scale) of magnetic particles trapped within the magnetic particle-water solution in the system illustrated in FIGS. 1A and 1B. In FIG. 3A, the flow tube is closer to the right magnet. In FIG. 3B, the flow tube is approximately centered between the two magnets. In FIG. 3C, the flow tube is closer to the left magnet.

FIGS. 5A-5D are photoacoustic images (logarithmic scale) of magnetic particles trapped within the magnetic particle-ink-water solution in the system illustrated in FIG. 1. In FIGS. 5A and 5B, the flow tube is closer to the right magnet. In FIGS. 5C and 5D, the flow tube is closer to the left magnet. FIGS. 5A and 5C are images before subtraction of the ink background. FIGS. 5B and 5D and images are after subtraction of the ink background.

DETAILED DESCRIPTION OF THE INVENTION

The present invention provides a method and system for magneto-motive photoacoustic (mmPA) imaging that uses nanoparticles with combined strong magnetic and efficient optical absorption properties. The method and system provide for magneto-motive manipulation to differentiate a coupled contrast agent from background signals.

Magneto-Motive Photoacoustic Imaging Method

In one aspect, the invention provides a method for detecting and/or imaging magnetic target objects within a moving fluid. In one embodiment, the method includes (a) introducing a plurality of magnetic particles having photoacoustic properties to a moving fluid comprising target objects to provide magnetically-labeled target objects;

(b) applying a magnetic field to an area of interest through which the fluid flows to accumulate the magnetically-labeled target objects in the area of interest to provide accumulated magnetically-labeled target objects in a first position;

(c) measuring a first photoacoustic signal from the accumulated magnetically-labeled target objects in the first position;

(d) manipulating the magnetic field in the area of interest to move at least a portion of the accumulated magnetically-labeled target objects in a predetermined pattern directly related to the magnetic field manipulation (e.g., to provide accumulated magnetically-labeled target objects in a second position); and (e) measuring one or more photoacoustic signals from the accumulated magnetically-labeled target objects during and/or after magnetic field manipulation.

In one embodiment, measuring one or more photoacoustic signals from the accumulated magnetically-labeled target objects during and after magnetic field manipulation includes measuring a sequence of photoacoustic signals from the accumulated magnetically-labeled target objects during and after magnetic field manipulation. In one embodiment, the one or more photoacoustic signals are measured during and immediately after magnetic field manipulation.

In one embodiment, the method further includes comparing the sequence of photoacoustic signals during magnetic field manipulation to provide a background suppressed photoacoustic signal. Comparing the sequence of photoacoustic signals during magnetic field manipulation provides a background suppressed photoacoustic image of the accumulated magnetically-labeled target objects.

In one embodiment, manipulating the magnetic field provides for the acquisition of photoacoustic signals from the accumulated magnetically-labeled target objects at two separate spatial locations. In this embodiment, comparing the photoacoustic signals acquired from the accumulated magnetically-labeled target objects at two separate spatial locations provides a background suppressed photoacoustic signal. Comparing the photoacoustic signals acquired at two separate spatial locations provides a background suppressed photoacoustic image of the accumulated magnetically-labeled target objects.

In the method, applying a magnetic field to an area of interest can include situating at least one magnet in a location sufficiently proximate to the area of interest to subject the area to an effective magnetic field. In one embodiment, a uniform polarizing magnetic field is applied in one direction (e.g., primarily) and combined with a collection of superimposed magnetic fields with significant spatial gradients in the component aligned with the direction of the polarizing magnetic field. In one embodiment, three mutually orthogonal gradient fields are applied.

In the method, any of the applied magnetic fields can be permanent or time varying.

In the method, the magnetic field can be manipulated by physically moving all or part of the magnets. Alternatively, the magnetic field can be manipulated by changing currents in electromagnets providing all or part of the applied fields. In certain embodiments, manipulating the magnetic field includes physically moving all or part of the magnets producing the gradient fields. Alternatively, the magnetic field can be manipulated by changing currents in electromagnets providing all or part of the gradient fields.

In one embodiment, photoacoustic signals are generated by delivering at least one laser pulse to the area of interest effective to generate the signal from the accumulated magnetically-labeled target objects. The first and second photoacoustic signals are generated by delivering at least one laser pulse to the areas of interest (e.g., first and second positions, respectively). In one embodiment, a single element ultrasonic transducer is used to record the photoacoustic signals. In other embodiments, one-dimensional or two-dimensional ultrasonic array transducers are used to record the photoacoustic signals.

In one embodiment, the method includes introducing a plurality of magnetic particles having photoacoustic properties to a moving fluid comprising target objects to provide magnetically-labeled target objects, applying a magnetic field to an area of interest through which the fluid flows to accumulate the magnetically-labeled target objects in the area of interest to provide magnetically-labeled target objects accumulated at a first position, measuring a first photoacoustic signal from the magnetically-labeled target objects accumulated at the first position, manipulating the magnetic field in the area of interest to accumulate at least a portion of the magnetically-labeled target objects at a second position, and measuring a second photoacoustic signal from the magnetically-labeled target objects accumulated at the second position. In this embodiment, first photoacoustic signal is measured once the labeled-target objects are accumulated in a first position. See FIG. 1A. After acquisition of the first photoacoustic signal, the magnetic field is manipulated to accumulate at least a portion of the labeled target objects in a second position in the area of interest that is different from the first position. See FIG. 1B. Magnetic field manipulation can be achieved by relocation of the magnet or altering the field strength relative to the area of interest causing at least a portion of the accumulated labeled target objects in the first position to accumulate in the second position. Once the labeled target objects are accumulated in the second position, a second photoacoustic signal is measured. In this embodiment, comparing the first and second photoacoustic signals provides a background suppressed photoacoustic signal (comparing the first and second photoacoustic signals comprises subtracting one signal from the other to provide a background suppressed photoacoustic image of the accumulated magnetically-labeled target objects).

By using an external magnetic field to manipulate magnetically-labeled target objects, the labeled target objects may be enriched, sorted, separated, captured, and/or immobilized as they are carried into the area of interest by the moving fluid. For example, the labeled target objects may be locally concentrated within the area of interest for imaging, significantly enhancing the detection sensitivity of the device, which is particularly effective when the labeled target objects occur at extremely low concentrations within the moving fluid.

In the method of the invention, the magnetically-labeled target objects are detected at a detection sensitivity ranging from about 1 to about 100 target objects per L of the moving fluid.

For biological applications, introducing the plurality of magnetic particles having photoacoustic properties to a moving fluid comprises administering the magnetic particles intravenously to a subject to be evaluated for the presence of target objects. In this embodiment, the magnetic particles can be administered together with a pharmaceutically acceptable carrier.

In other embodiments, the method further includes subjecting the accumulated magnetically-labeled target objects to an additional process selected from removal for biochemical or genetic analysis; non-invasive eradication using high-energy pulses selected from laser pulses, microwave pulses, or ultrasound pulses; magnetic purging; mechanical removal; needle extraction; and combinations thereof.

Magnetic Particles.

In the above methods, the magnetic particles have photoacoustic properties and are capable of binding to target objects. Suitable magnetic particles include microparticle complexes and nanoparticle complexes. Representative magnetic particles include from metal-magnetic complexes, carbon nanostructure-magnetic complexes, and mixtures thereof.

In certain embodiments, the magnetic particles having photoacoustic properties are metal-coated nanostructures. Suitable metal-coated nanostructures include those described in WO 2011/006002, expressly incorporated herein by reference in its entirety.

Representative metal-coated nanostructure includes a nanostructure core and a metal shell surrounding the core. In certain embodiments, the metal-coated nanostructure includes a cationic polymer intermediate the core and the shell that provides a spacing or gap between the core and the shell. Representative nanostructures include carbon nanotubes as well as other carbon nanoshaped-structures (e.g., nanospheres, nanoshells, nanorods, nanohorns, nanostars), quantum dots (i.e., semiconductor nanoparticles), metal nanoparticles, metal oxide nanoparticles, metalloid nanoparticles, metalloid oxide nanoparticles, polymer nanoparticles, silica nanoparticles, nanoscale micelles, nanoscale liposomes, and clusters and combinations thereof. As used herein, the term "nanoscale" refers to a particle having at least on nanoscale (up to 1000 nm) dimension.

In one embodiment, the nanoparticle is a magnetic nanoparticle. Suitable magnetic nanoparticles include particles that are responsive to a magnetic field. Representative magnetic nanoparticles include particles that include a suitable metal or metal oxide. Suitable metals and metal oxides include iron, nickel, cobalt, iron platinum, zinc selenide, ferrous oxide, ferric oxide, cobalt oxide, aluminum oxide, germanium oxide, tin dioxide, titanium dioxide, gadolinium oxide, indium tin oxide, cobalt iron oxide, magnesium iron oxide, manganese iron oxide, and mixtures thereof. Representative magnetic nanoparticles include metal nanoparticles, metal oxide nanoparticles, metalloid nanoparticles, and metalloid oxide nanoparticles. In certain embodiments, the metal and metal oxide nanoparticles are selected from gold, silver, copper, titanium, and oxides thereof. In other embodiments, the metal and metal oxide nanoparticles are lanthanide series metal nanoparticles.

In other embodiments, the magnetic particles having photoacoustic properties are nanostructures having magnetic particles attached thereto. Suitable such nanostructures include those described in WO 2011/006002, expressly incorporated herein by reference in its entirety. Representative nanostructures having magnetic particles attached thereto include a nanostructure core and a plurality of magnetic nanoparticles attached to the core. Suitable nanostructure cores and magnetic nanoparticles include those noted above for metal-coated nanostructures.

Other suitable nanostructures useful in preparing the magnetic nanoparticles useful in the method of the invention include those described in H. Wang, D. W. Brandl, F. Le, P. Nordlander, and N. J. Halas, "Nanorice: a hybrid plasmonic nanostructure," *Nano Letters* 6, 827-832 (2006); E. V. Shevchenko, M. I. Bodnarchuk, M. V. Kovalenko, D. V. Talapin, R. K. Smith, S. Aloni, W. Heiss, and A. P. Alivisatos, "Gold/iron oxide core/hollow-shell nanoparticles," *Adv. Mater.* 20, 4323-4329 (2008); L. Y. Wang, J. W. Bai, Y. J. Li, and Y. Huang, "Multifunctional nanoparticles displaying magnetization and near-IR absorption," *Angew. Chem. Int. Ed.* 47, 2439-2442 (2008); A. Gole, J. W. Stone, W. R. Gemmill, H. C. zur Loye, and C. J. Murphy, "Iron oxide coated gold nanorods: synthesis, characterization, and magnetic manipulation," *Langmuir* 24, 6232-6237 (2008); M. N. Hansen, L. S. Chang, and A. Wei, "Resorcinarene-encapsulated gold nanorods: solvatochromatism and magnetic nanoshell formation," *Supramol. Chem.* 20(1-2), 35-40 (2008); C. Wang and J. Irudayaraj, "Multifunctional magnetic-optical nanoparticle probes for simultaneous detection, separation, and thermal ablation of multiple pathogens," *Small* 6(2), 283-289 (2010); and C. Wang, J. Chen, T. Talavage, and J. Irudayaraj, "Gold nanorod/Fe3O4 nanoparticle "nano-pearl-necklaces" for simultaneous targeting, dual-mode imaging, and photothermal ablation of cancer cells," *Angew. Chem. Int. Ed.* 48, 2759-2763 (2009), each expressly incorporated herein by reference in its entirety.

To effect labeling to target objects, the magnetic particles having photoacoustic properties include one or more targeting moieties for selective binding to the target object. As used herein, the term "targeting moiety" refers to a chemical moiety associated with (i.e., covalently coupled or otherwise stably associated with the particle) that directs the particle to a specific site where the particle can then be imaged. Suitable targeting moieties include those known in the art. Representative targeting moieties are one of a binding pair. In one embodiment, the targeting moiety is an antibody or fragment thereof or its antigen. The antigen can be a small molecule, peptide, protein, polynucleotide, or polysaccharide. In one embodiment, the targeting moiety is a nucleic acid or its complement. The nucleic acid can be a DNA or an RNA. In one embodiment, the targeting moiety is an enzyme or its substrate. In one embodiment, the targeting moiety is a receptor or its ligand. In one embodiment, the targeting moiety is a nucleic acid or its partner protein. In one embodiment, the targeting moiety is a ligand for a cell, a cell membrane, or an organelle.

Representative targeting moieties include antibodies, ligands, antigens, or cell marker proteins.

Target Objects.

In the method of the invention, magnetic particles having photoacoustic properties interact with target objects in a moving fluid to provide magnetically-labeled target objects. Suitable target objects include biomarkers, therapeutic drugs, toxins, microparticles, nanoparticles, viruses, and cells.

Representative cells include abnormal cells, such as pathogenic bacteria, pathogenic fungal cells, pathogenic protists, sickle cells, inflamed cells, and cancer cells. In one embodiment, cancer cells include metastatic cancer stem cells. Metastatic cancer stem cells include those that result from a cancer selected from melanoma, leukemia, brain cancer, breast cancer, colon cancer, prostate cancer, ovarian cancer, pancreatic cancer, and testicular cancer.

Representative biomarkers include proteins, antibodies, hormones, single-stranded DNA fragments, double-stranded DNA fragments, or RNA fragments.

Fluid Media.

In the method of the invention, the magnetic particles having photoacoustic properties label target objects in a moving fluid. In one embodiment, the fluid is a biofluid of a living organism. Representative biofluids include blood, lymph, cerebrospinal fluid, urine, chyme, cytosol, tears, and interstitial fluid.

For fluids that are biofluids, the area of interest through which the fluid flows can be a circulatory vessel. Representative circulatory vessels include blood vessels, lymphatic vessels, extracorporeal shunts, and combination thereof.

Magnets.

In the method, applying a magnetic field to an area of interest comprises situating at least one magnet in a location sufficiently proximate to the area of interest to subject the area to an effective magnetic field. Representative useful magnets include permanent and pulsed magnets.

The magnet may be any existing permanent magnet or electromagnet capable of producing a steady or pulsed magnetic field at the magnet surface of at least 0.1 Tesla (T). In certain embodiments, the magnetic field strength at the magnet surface may be from about 0.1 T to about 20 T, from about 0.5 T to about 1 T, from about 0.75 T to about 1.5 T, from about 1 T to about 2 T, from about 2 T to about 4 T, from about 4 T to about 6 T, from about 6 T to about 8 T, from about 8 T to about 10 T, from about 10 T to about 12 T, from about 12 T to about 14 T, from about 14 T to about 16 T, from about 16 T to about 18 T, and from about 18 T to about 20 T. The strength of the magnetic field at the magnetic surface may be selected to be sufficiently strong to capture the labeled target objects moving through the area of interest. The strength of the magnetic field sufficient for the capture of moving target objects may be influenced by any one or more of at least several factors including, but not limited to, the size of the circulatory vessel through which the fluid may flow, the depth of the circulatory vessel relative to the skin surface of the organism, the flow speed of the fluid through the area of interest, the separation distance between the magnet and the area of interest, the duration of the magnetic pulse produced by a pulsed electromagnet, the intrinsic magnetic properties of the labeled target object, and the amount of magnetic material used to label the target object, among other factors.

The magnet may be constructed using any known magnetic material including hematite ($Fe_2O_3$), magnetite ($Fe_3O_4$), manganese-zinc ferrite ($Mn_aZn(1-a)Fe_2O_4$), nickel-zinc ferrite ($Ni_aZn(1-a)Fe_2O_4$), barium oxide, strontium oxide, and combinations thereof. In one embodiment, the magnet may be a cylindrical neodymium-iron-boron (NdFeB) magnet with Ni—Cu—Ni coating. Any known electromagnet may be used including resistive electromagnets and superconducting magnets.

Magneto-Motive Photoacoustic Imaging System

In another aspect, the invention provides a system for the manipulation, detection, and imaging of a magnetically-labeled target object within a moving fluid. In one embodiment, the system includes one or more first magnets effective for establishing a magnetic field in an area of interest within the moving fluid containing magnetically-labeled target objects; one or more second magnets effective for establishing a magnetic field including both a polarizing field and gradient fields in an area of interest within the moving fluid containing magnetically-labeled target objects; one or more energy sources for delivering incident energy to the accumulated magnetically-labeled target objects in the area of interest; and one or more photoacoustic transducers for receiving the photoacoustic signal from the accumulated magnetically-labeled target objects.

The magnetic field generated by first magnet or magnets is effective to accumulate the magnetically-labeled target objects in the area of interest. The magnetic field generated by the second magnet or magnets is effective to move accumulated magnetically-labeled target objects from a first position to a second position within the area of interest. The incident energy-generated by the energy source or sources is effective to generate a photoacoustic signal from the labeled target objects in the area of interest. The photoacoustic transducer is effective to receive a signal from the area of interest sufficient to image the labeled target objects.

Suitable magnets useful in the system include those known in the art and described above. Suitable photoacoustic transducers useful in the system include those know in the art. Representative photoacoustic transducers include single element ultrasonic transducers, one-dimensional ultrasonic array transducers, and two-dimensional ultrasonic array transducers.

Figure 1A:
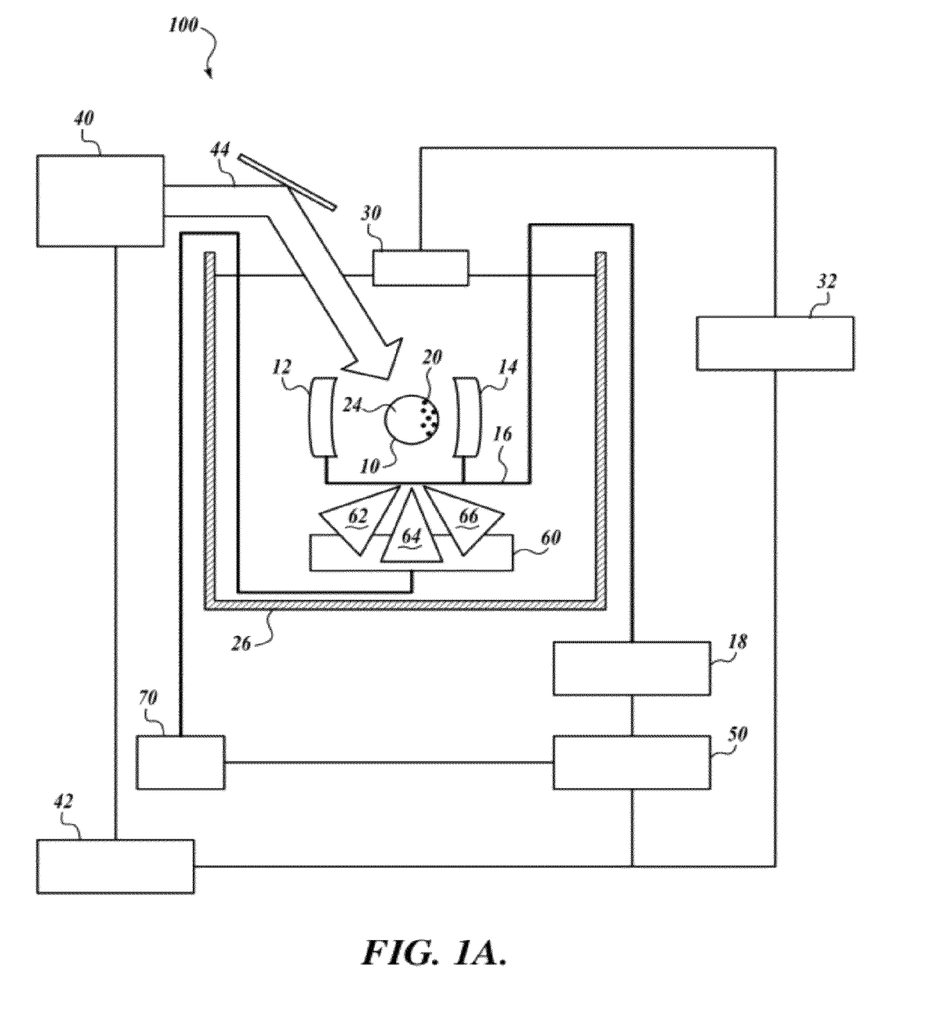
FIGS. 1A and 1B are schematic illustrations of a representative system of the invention for suppressing background signal in magneto-motive photoacoustic imaging of magnetic contrast agents in a fluid. The system includes a flow tube, first and second magnets for target object manipulation, a laser, and an ultrasound imaging transducer.
Figure 1B:
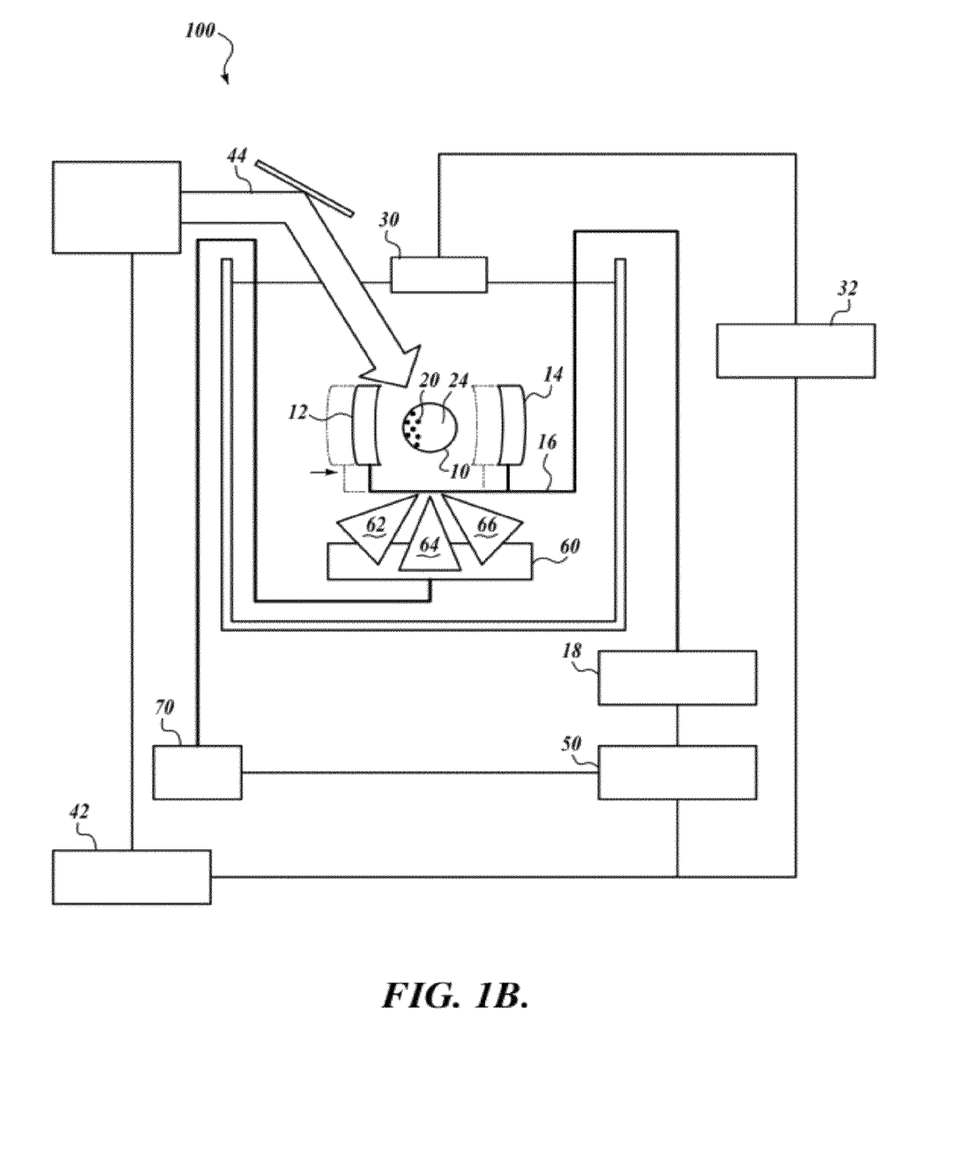

A representative system of the invention for suppressing background signal in magneto-motive photoacoustic imaging of magnetic contrast agents in a fluid is illustrated schematically in FIGS. 1A and 1B. The system 100 includes a flow tube 10 through which flows fluid 24 containing magnetically-labeled target objects 20; first magnets 12 and 14 associated with X-Y stage 16 and its controller 18 for translating the first magnets and manipulating the magnetic field within the flow tube; second magnets 62, 64, 66 (cone magnets in array 60) associated with its controller 70 for translating the second magnets along the flow tube and manipulating the magnetic field within the flow tube; laser 40 and associated controller 42 for delivering incident laser energy 44 to the labeled target object in the flow tube (reflective positioning mirror shown); ultrasound (photoacoustic) imaging transducer 30 (associated controller/processor 32) that is scanned to produce an array (e.g., a one-dimensional array) used for image reconstruction. The laser, ultrasound transducer, and first and second magnets can be synchronized through controller/processor computer 50. In this embodiment of the system, the first and second magnets and flow tube are in water contained by vessel 26. In FIG. 1A, the magnetically-labeled target objects are accumulated at a first position. In FIG. 1B, the magnetically-labeled target objects are accumulated at a second position.

In one embodiment, the system has the form of a cuff adapted to receive or conform to a suitable body part (e.g., arm, finger, leg, toe, wrist, elbow, shoulder, ankle, hip, knee, neck).

The following is a description of a representative method and system of the invention useful for mmPA imaging of targeted objects. The representative method and system are described in the Example below.

Manipulation of Magnetic Particles

The method and system of the present invention demonstrates that a mmPA system can trap and photoacoustically detect targeted objects in a circulating system. The total amount of trapped particles is determined by multiple physical effects, including the drag force from flow and the magnetic force between the magnets and the MPs. The method and system further demonstrates that targeted magnetic particles can be dynamically manipulation.

Figure 3A:
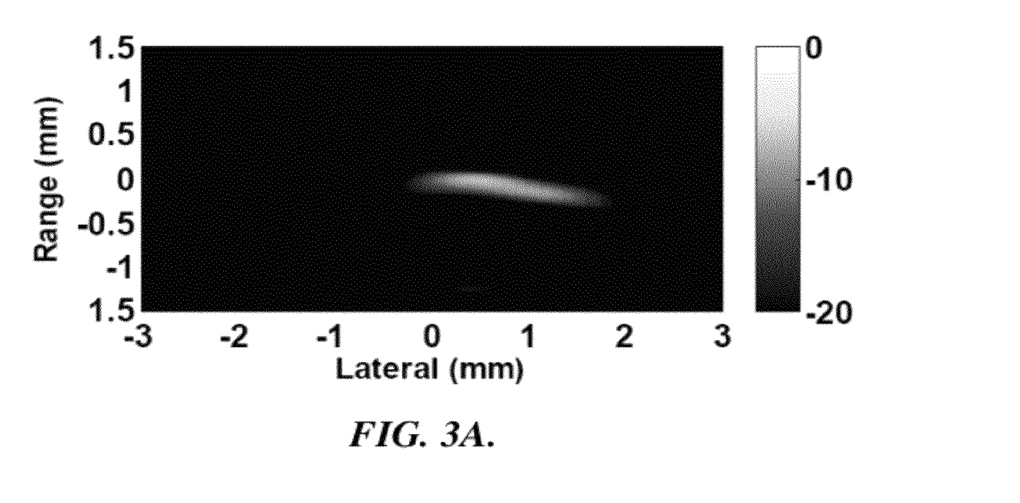

In the representative system, a flow tube was positioned closer to one (right) magnet and remained stationary for a period sufficient to accumulate representative target objects (magnetic particles, MPs) in a region near the right wall of the tube. There was no flow in the tube, so the number of accumulated MPs is directly related to the number of particles in that region of the system. After accumulation, PA measurements were performed. FIG. 3A presents the reconstructed image for the first tube position. Referring to FIG. 3A, the MPs are clearly observed on the right side of the tube. Note that the laser fluence used for medium irradiation was a hundred times smaller than medically-permitted norms, which renders the use of PVDF-based detection systems in vivo promising where strong light scattering is present from biological tissues and organs.

Figure 3B:
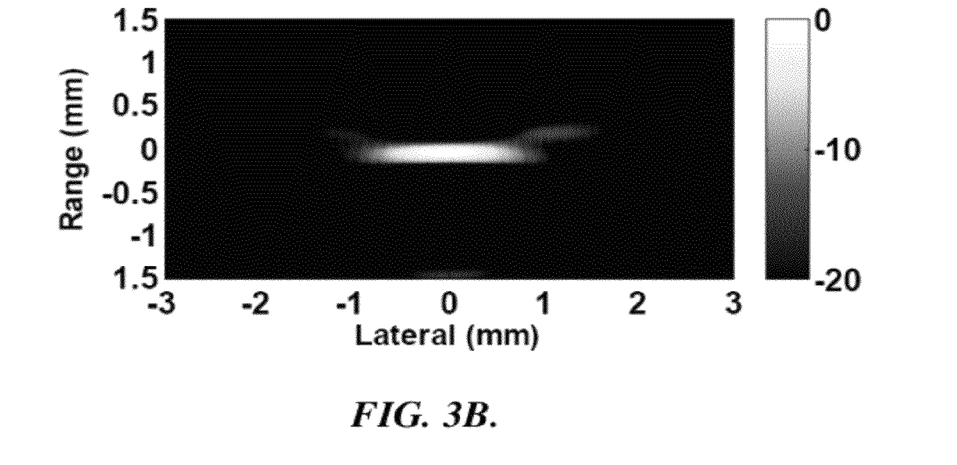
Figure 3C:
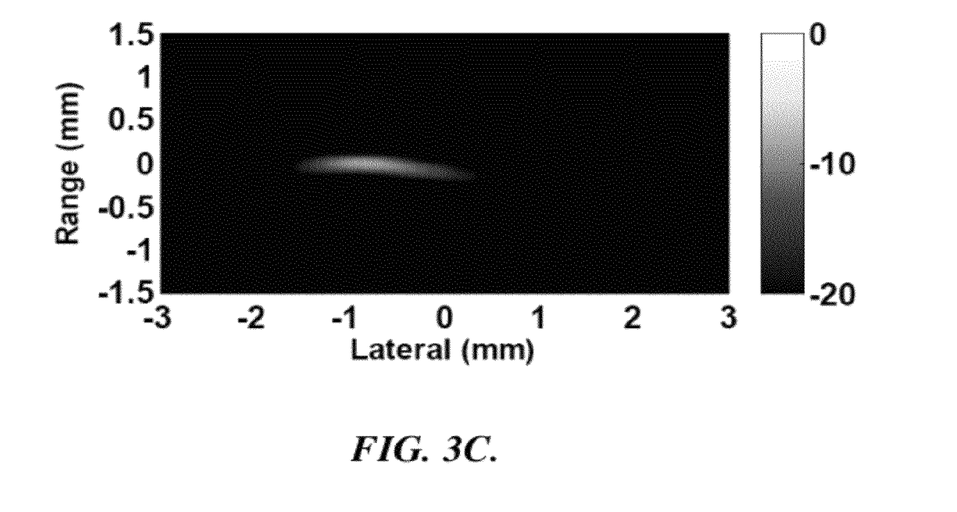

FIGS. 3B and 3C are images corresponding to the cases where the tube is positioned approximately centrally between the magnets and closer to the second (left) magnet, respectively. These images clearly demonstrate dynamic manipulation of large (μm scale) particles in mmPA imaging.

Suppression of the Background Signal

The method and system of the invention provide for suppression of background signal. Strong background signal produced by blood, which is always present together with any contrast agent and can produce much stronger PA signals than those of contrast agents, can be greatly suppressed using magnetic manipulation of the contrast agent. A small amount of ink was added to the initial MP-water solution to mimic a blood background. The system design was used to image the flow tube filled only with an ink-water solution without magnetic particles (i.e., background) and contrast that image to a set of images of the MP-ink-water solution.

Figure 4:
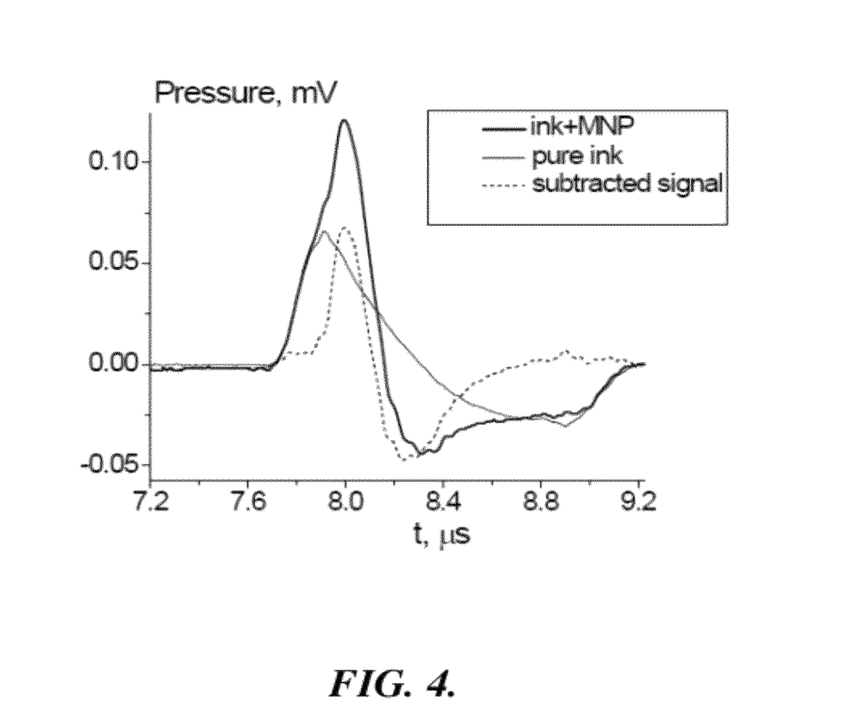
FIG. 4 is a graph illustrating temporal profiles of the detected signals for a pure ink-water solution (thin solid line, pure ink), magnetic particle-ink-water solution (bold solid line, ink+MNP), and their difference (dashed line, subtracted signal).

FIG. 4 shows the temporal profiles of the detected PA signals corresponding to the central position of the PVDF transducer (above the tube). Referring to FIG. 4, the thin solid curve corresponds to the temporal profile of the PA signal in the ink-water solution without magnetic particles; the bold solid curve represents the PA signal profile after magnetic particles are allowed to accumulate in the MP-ink-water solution with the tube in the center position of the magnets; and the differential signal is calculated as the difference of the first two (i.e., subtracting the signal excited in the ink-water solution from the signal excited in the MP-ink-water solution). As seen, the signal induced by the ink background is similar in both magnitude and time response to the signal produced by only the trapped MPs. The differential signal demonstrates almost perfect subtraction of the background.

In most biomedical applications (e.g., in vivo real-time monitoring) it is very difficult, or almost impossible, to obtain get a stable and reliable background signal. The present invention addresses this problem, through the use of a mmPA method, which in simplest form simply subtracts two PA images corresponding to two different magnet positions. Presumably, the background signal does not change with magnet position, so only the signal from targeted MPs should remain.

Figure 5A:
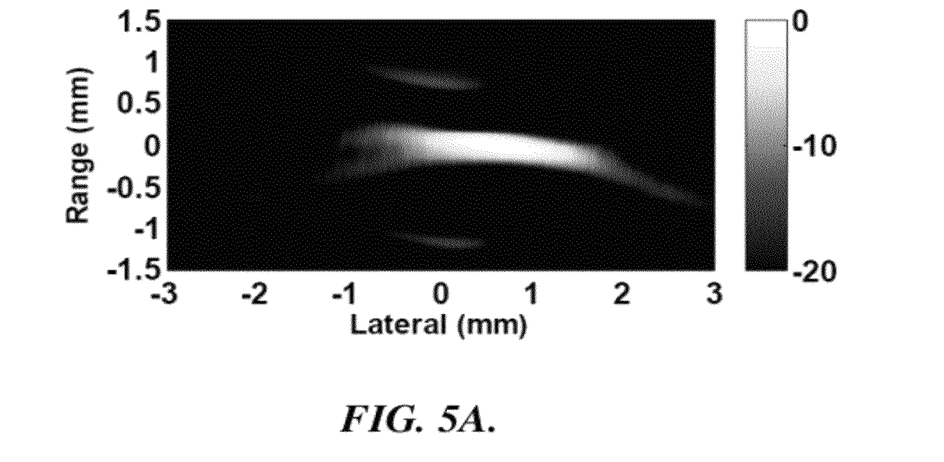
Figure 5B:
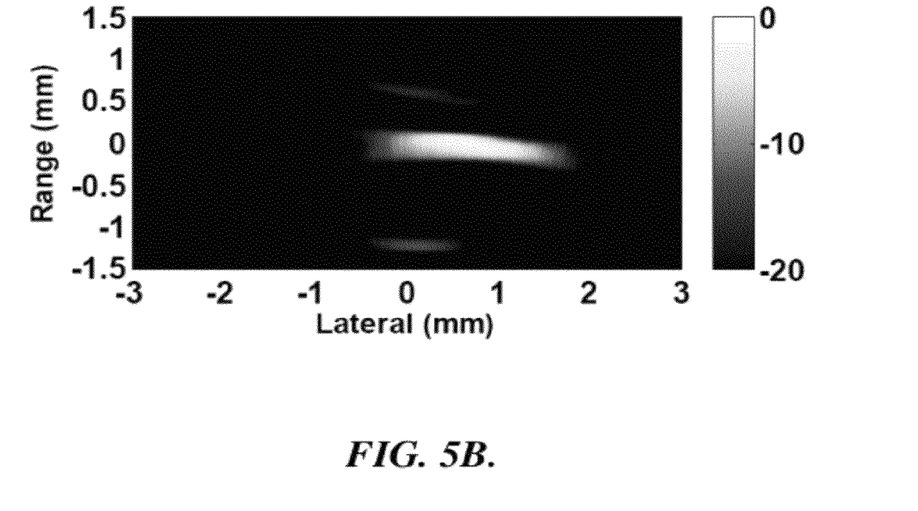
Figure 5C:
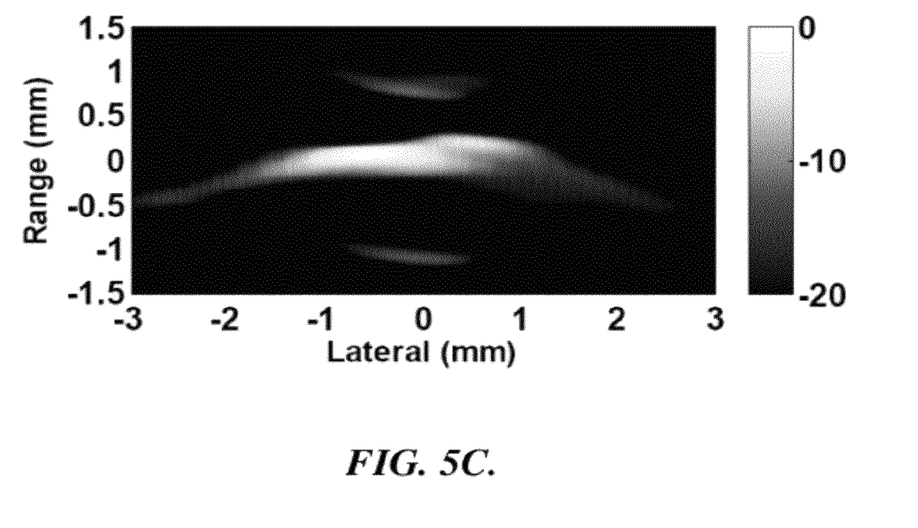
Figure 5D:
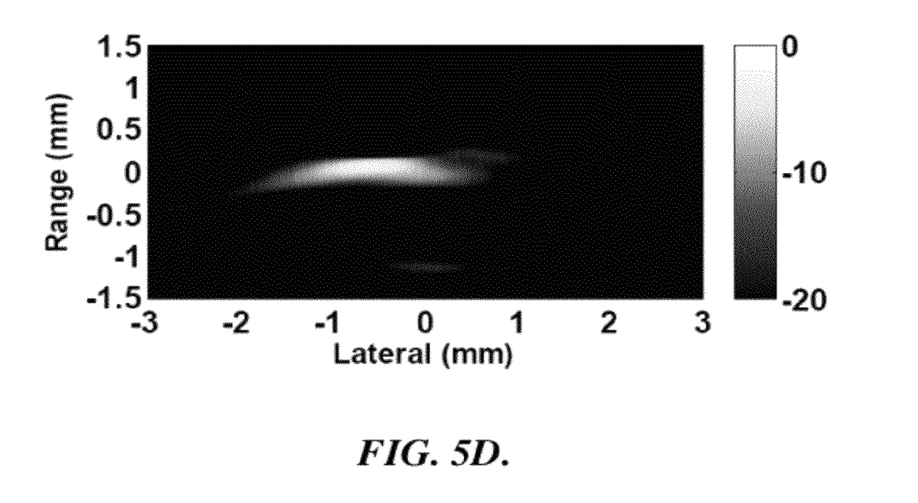

Images of MPs at two different magnet positions in the presence of the ink background are presented in FIGS. 5A and 5C. The differential images obtained after the subtraction of the ink background for the same magnet positions are shown in FIGS. 5B and 5D, respectively. Clearly, with the strong background signal from ink, it is very difficult to separate the contributions of the ink background and magnetic particles in the resulting images. These images are for a relatively large number of MPs in the imaging region. For a much smaller number of particles, similar to the case when a small number of targeted cells must be detected, it would be nearly impossible to uniquely detect the contribution from the contrast agent.

Figure 6:
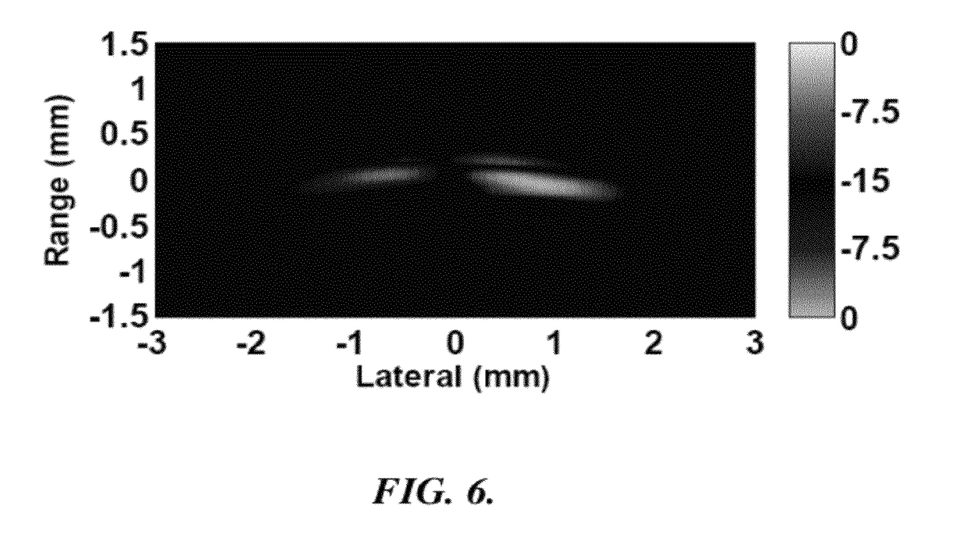
FIG. 6 is a differential image generated by subtracting the image of accumulated labeled target objects at a first position (FIG. 5C) from the image of accumulated labeled target objects at a second position (FIG. 5A) presented on a bipolar, logarithmic scale (the image of the flow tube with its left side close to the magnet subtracted from the image of the flow tube with its right side close to the magnet).

FIG. 6 illustrates the method and system of the invention: mmPA imaging using different particle locations induced by magneto-motive forces to suppress undesirable background signals. Referring to FIG. 6, a differential image is generated by subtracting the image for the flow tube position closer to the left magnet (FIG. 5C) from the image for the flow tube position closer to right magnet (FIG. 5A), and is displayed on a bipolar logarithmic scale to highlight the positions of the two locations while simultaneously suppressing the background ink signal.

Comparing the image of FIG. 6 to the component images in FIGS. 5A-5D and to the MP-water images in FIG. 3, the method and system of the invention provide for background suppression is substantial. However, complete suppression is not possible with a limited view transducer array because the induced artifacts depend on the positions of all sources in the reconstructed image. Only if the detecting surface represents a closed surface around the object under study, individual images, and thereby their difference, will be free from artifacts. The small lusterless spot in the upper right side of the differential image (FIG. 6) is most probably created by the superposition of artifacts inherent to individual images. Nevertheless, the results presented in FIG. 6 clearly demonstrate that even for a limited angle system, nearly complete suppression of the background is possible.

The method and system of the invention provide for effective magneto-motive manipulation of μm-scale magneto-sensitive particles mimicking targeted cells circulating in the vasculature. The results clearly indicate that the undesirable strong PA background signal can be effectively suppressed using the difference of PA images corresponding to different locations of accumulated particles.

The following example is provided for the purpose of illustrating, not limiting the invention.

Representative Magneto-Motive Photoacoustic Imaging System and Method

A representative magneto-motive photoacoustic imaging system was designed and constructed as illustrated schematically in FIGS. 1A and 1B. A Teflon tube (Zeus PTFE (Teflon) Sublite Wall Tubing, Seattle, Wash.) with an inner diameter of 1.65 mm and a wall thickness of 38 μm was positioned in a tank filled with deionized (DI) water to model a blood vessel. The tube was filled with a water-based, 0.05 mg/ml solution of BioMag® Superparamagnetic Iron Oxide (Polysciences, Inc., Warrington, Pa.) particles (MP) with a diameter of about 10 μm. These particles were used to mimic cells conjugated with magnetic nanoparticles and can be dynamically manipulated by two neodymium magnets (AY0X030-N and AY0X030-S, Jamison, Pa.). These magnets, separated by 4 cm with pole pieces 1.27 cm×2.54 cm in cross section were mounted into two aluminum frames to form a dual magnet system sitting on a translation stage so that they could be moved together laterally. The magnetic field was about 0.5 Tesla at the surface of each magnet and dropped to about 0.1 Tesla at the middle of the system.

An optical parametric oscillator (Surelite OPO Plus, Continuum, Santa Clara, Calif.) pumped by a frequency-doubled pulsed YAG laser (Surelite I-20, Continuum) with 5-ns pulse width was used as the laser source. The laser beam was guided to illuminate the imaged object from the top with a tilt angle of about 45 degrees as shown in FIGS. 1A-1B. The imaged objects were illuminated at a wavelength of 710 nm. The laser fluence at the tube surface was 0.36 mJ/cm$^2$. The absorption spectrum for the MP is peaked in the visible range and is greatly reduced from this peak for near infrared wavelengths. Nevertheless, there was sufficient absorption at 710 nm to demonstrate the principle of magnetic manipulation with PA readout.

Excited PA signals were detected with a single-channel thin strip polyvinylidene fluoride (PVDF) transducer. The film thickness of 110 μm allowed highly-sensitive signal detection (about 0.6 mV/Pa using 30-fold amplification) with practically flat efficiency in the frequency range of 100 kHz-8 MHz. The sensitive area of the transducer was made as a thin strip with dimensions of 0.6 mm×7 mm. The long axis was aligned along the tube direction to provide maximum spatial resolution in axial and lateral directions. Multi-channeled PA detection was performed by scanning the transducer laterally to synthesize a one-dimensional array. One hundred twenty (120) transducer positions separated by 0.4 mm were used for image reconstruction. The inverse problem of PA tomography is the reconstruction of the laser induced heat release Q($\vec{r}$), if the value of the Gruneizen parameter Γ for the medium is known, from the PA signals measured, ideally, at each point of a detection surface. This problem has a unique solution and can be written in integral form for the three most widespread detection surfaces: a confined sphere, an infinite cylinder, and an infinite plane. This problem can be treated in either time or spatial frequency domains. See, for example, M. Xu, Y. Xu, L. V. Wang, "Time-Domain Reconstruction Algorithms and Numerical Simulations for Thermoacoustic Tomography in Various Geometries", *IEEE Trans. On Biomed. Eng.*, 50(9), 1086-1099 (2003); and K. P. Kostli, M. Frenz, H. Bebie, H. P. Weber, "Temporal backward projection of optoacoustic pressure transients using Fourier transform methods", *Phys. Med. Biol.*, 46, 1863-1872 (2001).

The resulting expression for the reconstructed distribution of the heat release in the time-domain consists of the integral over the detection surface of the negative of the temporal derivative of the detected signals. A more detail description of the inverse problem of PA tomography is described in See, for example, M. Xu, Y. Xu, L. V. Wang, "Time-Domain Reconstruction Algorithms and Numerical Simulations for Thermoacoustic Tomography in Various Geometries", *IEEE Trans. On Biomed. Eng.*, 50(9), 1086-1099 (2003); T. D. Khokhlova, I. M. Pelivanov, V. V. Kozhushko, A. N. Zharinov, V. S. Solomatin, A. A. Karabutov "Optoacoustic imaging of absorbing objects in a turbid medium: ultimate sensitivity and application to breast cancer diagnostics", *Applied Optics* 46(2), 262-272 (2007); and T. Khokhlova, I. Pelivanov, A. Karabutov, "Advances in Optoacoustic Imaging", Chapter 13 in *Handbook of Photonics in Biomedical Science*, edited by V. Tuchin, CRC Press, 2010.

Unfortunately, if the detection surface is not confined or even if limited view linear arrays detectors are employed for the reconstruction, the imaged distribution of heat release is not free of artifacts. The most important artifact is the expansion of the reconstructed object in the lateral direction due to limited view detection.

In the representative system, the flow tube with the MP solution was placed at a distance of 40 mm from the detection line. Given a total array aperture of 48 mm (120 steps), the reconstruction corresponded to a total detection angle of approximately 62 degrees.

Figure 2:
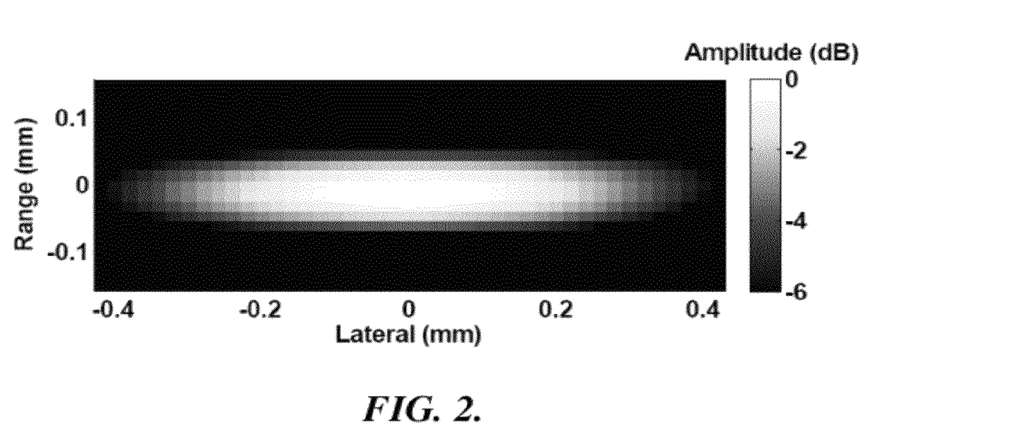
FIG. 2 is an image of a point spread function of a polyvinylidene fluoride (PVDF) transducer array using the signal processing parameters as described in Example 1.

The point spread function (PSF) of the system was measured by reconstructing the image of a human hair placed in the same position as the flow tube in further experiments. As seen in FIG. 2, the axial resolution of the reconstructed PSF of the imaging system is determined by the bandwidth of the transducer used for the detection and is equal to approximately 80 μm. The resolution in the lateral direction is much worse at about 650 μm, resulting from the finite width of an individual array element and the limited observation angle of the total array.

First, to demonstrate the principle of particle trapping and manipulation, a solution of magnetic particles in water (concentration given above) was used. To more closely mimic the in vivo situation of particles trapped in blood, a small amount of ink was added to the initial solution to form a MP-ink-water solution. This medium was used to test the principle of background subtraction through magnetic manipulation of trapped particles. The concentration of ink in the resulting solution was chosen to provide a light absorption coefficient of 5 $cm^{-1}$, corresponding to expected light absorption of blood in a human vessel in the near infrared region.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for detecting magnetic target objects within a moving fluid, comprising:
   (a) introducing a plurality of magnetic particles having photoacoustic properties to a moving fluid comprising target objects to provide magnetically-labeled target objects;
   (b) applying a magnetic field to an area of interest through which the fluid flows to accumulate the magnetically-labeled target objects in the area of interest to provide accumulated magnetically-labeled target objects in a first position;
   (c) measuring a first photoacoustic signal from the accumulated magnetically-labeled target objects in the first position;
   (d) manipulating the magnetic field in the area of interest to move at least a portion of the accumulated magnetically-labeled target objects in a predetermined pattern directly related to the magnetic field manipulation; and
   (e) measuring one or more photoacoustic signals from the accumulated magnetically-labeled target objects during and after magnetic field manipulation.

2. The method of claim 1, wherein measuring one or more photoacoustic signals from the accumulated magnetically-labeled target objects during and after magnetic field manipulation comprises measuring a sequence of photoacoustic signals from the accumulated magnetically-labeled target objects during and after magnetic field manipulation.

3. The method of claim 1, wherein measuring one or more photoacoustic signals from the accumulated magnetically-labeled target objects during and after magnetic field manipulation comprises measuring one or more photoacoustic signals from the accumulated magnetically-labeled target objects during and immediately after magnetic field manipulation.

4. The method of claim 1 further comprising comparing the sequence of photoacoustic signals during magnetic field manipulation to provide a background suppressed photoacoustic signal.

5. The method of claim 4, wherein comparing the sequence of photoacoustic signals during magnetic field manipulation provides a background suppressed photoacoustic image of the accumulated magnetically-labeled target objects.

6. The method of claim 1, wherein manipulating the magnetic field results in acquiring photoacoustic signals from the accumulated magnetically-labeled target objects at two separate spatial locations.

7. The method of claim 6 further comprising comparing the photoacoustic signals acquired from the accumulated magnetically-labeled target objects at two separate spatial locations to provide a background suppressed photoacoustic signal.

8. The method of claim 7, wherein comparing the photoacoustic signals acquired at two separate spatial locations provides a background suppressed photoacoustic image of the accumulated magnetically-labeled target objects.

9. The method of claim 1, wherein applying a magnetic field to an area of interest comprises situating at least one magnet in a location sufficiently proximate to the area of interest to subject the area to an effective magnetic field.

10. The method of claim 9, wherein a uniform polarizing magnetic field applied primarily in one direction is combined with a collection of superimposed magnetic fields with significant spatial gradients in the component aligned with the direction of the polarizing magnetic field.

11. The method of claim 10, wherein three mutually orthogonal gradient fields are applied.

12. The method of claim 10, wherein any of the applied magnetic fields are permanent or time varying.

13. The method of claim 1, wherein measuring a first photoacoustic signal comprises delivering at least one laser pulse to the area of interest effective to generate a photoacoustic signal from the accumulated magnetically-labeled target objects at the first position.

14. The method of claim 1, wherein a single element ultrasonic transducer is used to record the photoacoustic signals.

15. The method of claim 1, wherein a one-dimensional or two-dimensional ultrasonic array transducer is used to record the photoacoustic signals.

16. The method of claim 1, wherein manipulating the magnetic field comprises physically moving all or part of the magnets.

17. The method of claim 1, wherein manipulating the magnetic field comprises changing currents in electromagnets providing all or part of the applied fields.

18. The method of claim 10, wherein manipulating the magnetic field comprises physically moving all or part of the magnets producing the gradient fields.

19. The method of claim 10, wherein manipulating the magnetic field comprises changing currents in electromagnets providing all or part of the gradient fields.

20. The method of claim 1, wherein measuring a second photoacoustic signal comprises delivering at least one laser pulse to the area of interest effective to generate a photoacoustic signal from the accumulated magnetically-labeled target objects during magnetic field manipulation.

21. The method of claim 1 further comprising subjecting the accumulated magnetically-labeled target objects to an additional process selected from removal for biochemical or genetic analysis; non-invasive eradication using high-energy pulses selected from laser pulses, microwave pulses, or ultrasound pulses; magnetic purging; mechanical removal; needle extraction; or any combination thereof.

22. The method of claim 1, wherein the magnetic particles having photoacoustic properties are nanoparticle complexes or a microparticle complexes selected from metal-magnetic complexes, quantum dot-magnetic complexes, carbon nanostructure-magnetic complexes, or mixtures thereof.

23. The method of claim 1, wherein the magnetic particles having photoacoustic properties are metal-coated nanostructures.

24. The method of claim 1, wherein the magnetic particles having photoacoustic properties comprise one or more targeting moieties for selective binding to the target object.

25. The method of claim 24, wherein targeting moieties are selected from antibodies, ligands, antigens, or cell marker proteins.

26. The method of claim 1, wherein the target objects are selected from biomarkers, therapeutic drugs, toxins, microparticles, nanoparticles, viruses, or cells.

27. The method of claim 26, wherein the biomarkers are selected from proteins, antibodies, hormones, single-stranded DNA fragments, double-stranded DNA fragments, or RNA fragments.

28. The method of claim 26, wherein the cells are abnormal cells.

29. The method of claim 26, wherein the cells are selected from pathogenic bacteria, pathogenic fungal cells, pathogenic protists, sickle cells, inflamed cells, or cancer cells.

30. The method of claim 29, wherein the cancer cells are metastatic cancer stem cells.

31. The method of claim 30, wherein the metastatic cancer stem cells result from a cancer selected from melanoma, leukemia, brain cancer, breast cancer, colon cancer, prostate cancer, ovarian cancer, pancreatic cancer, or testicular cancer.

32. The method of claim 1, wherein the fluid is a biofluid of a living organism.

33. The method of claim 32, wherein the biofluid is selected from blood, lymph, cerebrospinal fluid, urine, chyme, cytosol, tears, or interstitial fluid.

34. The method of claim 1, wherein the area of interest through which the fluid flows is a circulatory vessel.

35. The method of claim 34, wherein the circulatory vessel is selected from a blood vessel, a lymphatic vessel, an extracorporeal shunt, or any combination thereof.

36. The method of claim 1, wherein introducing the plurality of magnetic particles having photoacoustic properties to a moving fluid comprises administering the magnetic particles intravenously to a subject to be evaluated for the presence of target objects.

37. The method of claim 1, wherein the magnetically-labeled target objects are detected at a detection sensitivity ranging from about 1 to about 100 target objects per mL of the moving fluid.

38. A device for the manipulation and detection of a magnetically-labeled target object within a moving fluid, comprising:
(a) one or more first magnets effective for establishing a magnetic field in an area of interest within moving fluid containing magnetically-labeled target objects, wherein the magnetic field is effective to accumulate the magnetically-labeled target objects in the area of interest;
(b) one or more second magnets effective for establishing a magnetic field including both a polarizing field and gradient fields in an area of interest within moving fluid containing magnetically-labeled target objects, wherein the magnetic field is effective to move accumulated magnetically-labeled target objects from a first position to a second position within the area of interest;
(c) one or more light energy sources for delivering incident energy to the accumulated magnetically-labeled target objects in the area of interest, wherein the incident energy is sufficient to generate a photoacoustic signal from the accumulated magnetically-labeled target objects; and
(d) one or more photoacoustic transducers for receiving the photoacoustic signal from the accumulated magnetically-labeled target objects.

39. The device of claim 38, wherein the first magnet is a permanent or pulsed magnet or electromagnet.

40. The device of claim 38, wherein the second magnet is a permanent or pulsed magnet or electromagnet.

41. The device of claim 38, wherein the first or second magnet comprises a magnetic material selected from the group consisting of hematite ($Fe_2O_3$), magnetite ($Fe_3O_4$), manganese-zinc ferrite ($Mn_aZn_{(1-a)}Fe_2O_4$), nickel-zinc ferrite ($Ni_aZn_{(1-a)}Fe_2O_4$), barium oxide, strontium oxide, and combinations thereof.

42. The device of claim 38, wherein the first or second magnet is a cylindrical neodymium-iron-boron (NdFeB) magnet with Ni—Cu—Ni coating.

43. The device of claim 38, wherein the light energy source is a laser.

44. The device of claim 38, wherein the light energy source is a pulse laser.

45. The device of claim 38, wherein the photoacoustic transducer is a single element ultrasonic transducer, a one-dimensional ultrasonic array transducer, or a two-dimensional ultrasonic array transducer.

46. The device of claim 38, wherein the device has the form of a cuff adapted to receive or conform to a suitable body part.

47. The device of claim 46, wherein the body part is selected from an arm, a finger, a leg, a toe, a wrist, an elbow, a shoulder, an ankle, a hip, a knee, or neck.

* * * * *